(12) United States Patent
Bieler et al.

(10) Patent No.: US 9,193,667 B2
(45) Date of Patent: Nov. 24, 2015

(54) PROCESS FOR THE SELECTIVE META-CHLORINATION OF ALKYLANILINES

(75) Inventors: Nikolaus Bieler, Brig-Glis (CH); Stefan Ellinger, Visp (CH); Martina Furrer, Visp (CH); Viktor Ladnak, Thun (CH); Constanze Müller, Naters (CH); Leo Schmid, Glis (CH); Cornelia Zur Täschler, Visp (CH)

(73) Assignee: LONZA LTD., Basel (CH)

( * ) Notice: Subject to any disclaimer, the term of this patent is extended or adjusted under 35 U.S.C. 154(b) by 73 days.

(21) Appl. No.: 13/817,972

(22) PCT Filed: Aug. 16, 2011

(86) PCT No.: PCT/EP2011/004099
§ 371 (c)(1),
(2), (4) Date: Aug. 28, 2013

(87) PCT Pub. No.: WO2012/022460
PCT Pub. Date: Feb. 23, 2012

(65) Prior Publication Data
US 2013/0338400 A1 Dec. 19, 2013

(30) Foreign Application Priority Data

Aug. 20, 2010 (EP) .................................... 10173496

(51) Int. Cl.
*C07C 209/00* (2006.01)
*C07C 209/74* (2006.01)

(52) U.S. Cl.
CPC .................................. *C07C 209/74* (2013.01)

(58) Field of Classification Search
CPC combination set(s) only.
See application file for complete search history.

(56) References Cited

U.S. PATENT DOCUMENTS 3,962,336 A 6/1976 Lademann et al.
4,401,833 A 8/1983 Schnegg et al.

FOREIGN PATENT DOCUMENTS

EP 0052817 A1 6/1982

OTHER PUBLICATIONS

Beard, C., et al., "Molecular Rearrangements. Part II. 2:6-Disubstituted N-Chloroacetanilides", J. Chem. Soc., 1958, pp. 2982-2986.

*Primary Examiner* — Clinton Brooks
(74) *Attorney, Agent, or Firm* — Hoffmann & Baron, LLP

(57) ABSTRACT

A process for the chlorination of alkylanilines is provided allowing a highly selective chlorination in the meta-position of the aromatic ring. This is achieved by reacting a mixture comprising the alkylaniline and sulfuric acid with chlorine. This process allows a meta-chlorination with a selectivity of more than 90%.

10 Claims, No Drawings

PROCESS FOR THE SELECTIVE META-CHLORINATION OF ALKYLANILINES

This application is the U.S. National Phase of, and Applicants claim priority from, International Application No. PCT/EP2011/004099 filed Aug. 16, 2011 and European Patent Application No. 10173496.0 filed Aug. 20, 2010, each of which is incorporated herein by reference.

BACKGROUND OF THE INVENTION

The present invention is directed to a process for the preparation of chlorinated alkylanilines, in particular chlorinated 2,6-dialkylanilines.

Meta-chlorinated 2,6-dialkylanilines are important starting materials for the preparation of chlorinated 4,4'-methylene-bis(2,6-dialkylanilines) which are used as chain extenders or cross linking agents in the polymer industry, for example in the preparation of polyurethanes and epoxy resins.

Beard and Hickinbottom (*J. Chem. Soc.*, 1958, 2982-2986) describe meta-selective chlorination of 2,6-dialkylanilines starting from the corresponding N-chloro-acetanilides. This reaction, however, suffers from the disadvantage of additional protection and deprotection steps in order to obtain the free amine.

U.S. Pat. No. 3,962,336 discloses the preparation of 5-chloro-2-toluidine by reacting 2-toluidine hydrochloride with chlorine. Direct chlorination of other anilines, however, leads to the formation of product mixtures as described in GB-A-1 521 136.

U.S. Pat. No. 4,401,833 discloses the direct chlorination of the hydrochlorides of 2,6-dialkylanilines in an organic solvent system, wherein the hydrochlorides are sparingly soluble. Consequently, the bulk of the hydrochloride is present in crystalline form as a suspension. This process, however, results in 4-chloro-2,6-dialkylanilines only.

The object of the present invention, therefore, is to provide an effective and cost efficient process for the meta-selective chlorination of alkylanilines, in particular 2,6-dialkylanilines.

DESCRIPTION OF THE INVENTION

This object has been achieved by a process for the preparation of chlorinated alkylanilines of the formula (1)

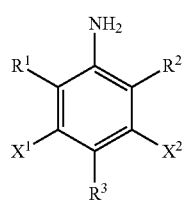

(1)

wherein $R^1$, $R^2$ and $R^3$ independently are H or an alkyl group, with the proviso that at least one of $R^1$ and $R^2$ is an alkyl group, and $X^1$ and $X^2$ independently are H or Cl, with the proviso that at least one of $X^1$ and $X^2$ is Cl, or a sulfuric acid salt thereof, said process comprising:

(a) providing an alkylaniline of the formula (2)

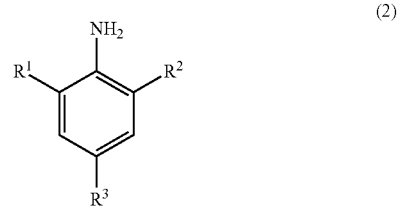

(2)

wherein $R^1$, $R^2$ and $R^3$ are as defined above, in the anilinium form in a mixture with sulfuric acid as solvent; and (b) treating the mixture of step (a) with chlorine ($Cl_2$) to obtain the alkylaniline of the formula (1) in the form of a sulfuric acid salt, optionally followed by treatment with a base to obtain the free alkylaniline.

It has been found that the process of the invention allows meta-chlorination of alkylanilines of the general formula (2) with high selectivity and in excellent yields by using sulfuric acid as solvent. Sulfuric acid is essentially the sole solvent, while organic solvents are preferably absent. Due to the higher solubility of anilinium sulfates in sulfuric acid (as compared to organic solvents) all, or at least a substantial part of, the anilinium salt is dissolved in the sulfuric acid.

The term alkyl as used in the definition of $R^1$, $R^2$ and $R^3$ includes linear and branched alkyl groups. Preferably, the alkyl group is a $C_{1-6}$ alkyl group, more preferably a $C_{1-4}$ alkyl group. Preferred alkyl groups include methyl, ethyl, n-propyl, isopropyl, n-butyl, sec-butyl and tert-butyl. More preferred alkyl groups are methyl, ethyl, n-propyl, isopropyl and sec-butyl. Most preferred alkyl groups represented by $R^1$, $R^2$ and $R^3$ are methyl, ethyl and isopropyl.

Preferably, the residues $R^1$ and $R^2$ in the compounds of the formula (1) and (2) independently represent an alkyl group. More preferably, $R^1$ and $R^2$ are the same.

In a particular preferred embodiment of the invention, $R^3$ in the compounds of the formulas (1) and (2) is H.

The sulfuric acid ($H_2SO_4$) used in the present process in admixture with the alkylaniline of the formula (2) preferably is a sulfuric acid having an acid concentration of at least 70% by weight, more preferably of at least 85% by weight, even more preferably of at least 90% by weight, and most preferably of at least 95% by weight. While meta-selectivity of the reaction is maintained even when sulfuric acid having an acid concentration of below 70% is used, yield is better at higher concentrations.

Typically, the alkylaniline of the formula (2) in its anilinium form is provided by mixing the aniline with sulfuric acid. Following mixing of the two components, the alkylaniline will essentially be present in the form a sulfuric acid salt, i.e., the anilinium sulfate and/or the anilinium hydrogensulfate, which will react with the chlorine. Advantageously, the sulfuric acid is used in a molar excess with respect to the alkylaniline. This allows better mixing and probably dissolution of the anilinium salt in the sulfuric acid. For improved yields, thus, the molar ratio of sulfuric acid to alkylaniline in the starting mixture preferably should be at least 1.8:1, more preferably at least 2.5:1. Molar ratios of sulfuric acid to alkylaniline of 20:1 and more will be possible but will not improve yield. Alternatively, the alkylaniline of the formula (2) can be provided in the form of an anilinium salt, preferably a sulfuric acid salt such as the anilinium hydrogensulfate or the anilinium sulfate, which is mixed with the sulfuric acid.

Chlorination of the alkylanilines of the formula (2) is effected using chlorine gas which is introduced into or passed through the mixture with the sulfuric acid. The reaction is typically carried out at a temperature in a range of from 5° C. to 120° C., preferably of from 10° C. to 100° C. Lower or higher temperatures may work as well, but lower temperatures may result in a decrease in the reaction rate while higher temperatures will not increase yield.

The product of the chlorination reaction essentially is the sulfuric acid salt of the chlorinated alkylaniline of the formula (1), i.e. the anilinium hydrogensulfate or the anilinium sulfate. The free chlorinated alkylaniline can be liberated from its salt by separating the sulfuric acid salts from the reaction mixture by crystallization followed by treatment with a base. Preferably, the reaction mixture containing the sulfuric acid and the sulfuric acid salts will be treated directly with the base to neutralize the sulfuric acid and to liberate the chlorinated alkylaniline. Bases which may be used for treatment include organic bases such as triethylamine and inorganic bases such as alkali metal hydroxides and carbonates. Sodium or potassium hydroxide are preferred and are typically used in the form of aqueous solutions.

The liberated chlorinated alkylaniline can be isolated according to known methods, for example by separating the organic layer or by extraction with a water immiscible solvent such as dichloromethane, ethyl acetate or toluene. The solvent may then be removed under reduced pressure. The chlorinated anilines may be purified by distillation.

The process of the invention may be carried out in a closed or in an open system.

According to a preferred embodiment of the invention, the chlorination reaction is carried out in a closed system, which has the advantage that it does not exchange matter with its surroundings during the reaction. Such a closed system may be a sealed reaction vessel such as a sealed autoclave. Use of a closed system allows easy control of the stoichiometry of the reactants. Typically, in the process of the invention the mixture of alkylaniline and sulfuric acid is charged into the reaction vessel, preferably an autoclave, and the reaction vessel is then sealed and the calculated amount of chlorine gas is added. Due to the use of a closed system, no reactants will leak so that a predetermined molar ratio of the reactants can be provided for controlling the process.

Alternatively, the chlorination reaction of the invention can be carried out in an open system which allows the flow of matter out of the system boundaries. The open system used in the process of the invention may be an open reaction vessel such as a standard glass apparatus which is charged with the alkylaniline and the sulfuric acid to which chlorine gas is added. Conveniently, the chlorine gas is passed through the reaction mixture, for example using a dip pipe.

The degree of chlorination may be controlled, for example, by adjusting the stoichiometry of the reactants, that is, the molar ratio of chlorine gas to alkylaniline of formula (2), the choice of the reaction system and the reaction temperature.

If the chlorination reaction is carried out in a closed reaction vessel, a meta-substituted mono-chlorinated product is obtained in high yields if chlorine ($Cl_2$) and alkylaniline are used in about stoichiometric amounts, i.e., if the molar ratio of chlorine molecules to alkylaniline is in the range of from 0.90:1 to 1.10:1, more preferably in the range of from 0.95:1 to 1.05:1. The reaction is preferably carried out within the temperature range given above. The reaction time usually is in a range of from 5 min to 10 h.

In the closed system, if the molar ratio of chlorine to alkylaniline is increased, the 3,5-dichlorinated alkylaniline tends to become the main product of the chlorination reaction.

Thus, if a 3,5-dichlorinated alkylaniline is desired, this can be achieved by increasing the amount of added chlorine. For obtaining a dichlorinated product, the molar ratio of chlorine to alkylaniline is thus increased to at least 2:1, more preferably to at least 3.5:1. Molar ratios exceeding 4.5:1 may not increase yield and/or may result in undesired side products such as higher chlorinated products. The reaction equilibrium may also be shifted to the dichlorinated reaction product by increasing the reaction temperature, for example within a range of from 60° C. to 90° C.

If the chlorination reaction is carried out in an open reaction vessel, the meta-substituted mono-chlorinated product is obtained in high yields if chlorine is passed through the reaction mixture. The dichlorinated compounds will be obtained only upon longer reaction times and by passing large amounts of chlorine through the reaction mixture.

In case the alkyl substituents of the anilines of the formula (2) are different, chlorination may result in different isomers. For example, if $R^1$ and $R^2$ are different alkyl groups and $R^3$ is H, two mono-chlorinated isomers will be obtained from which the predominant one is the isomer where the meta-position is sterically less hindered by the adjacent alkyl substituent. For example, when 2-isopropyl-6-methylaniline is chlorinated according to the process of the invention, a product mixture consisting of 3-chloro-6-isopropyl-2-methylaniline and 3-chloro-2-isopropyl-6-methylaniline is obtained in a ratio of about 4:1.

Preferably, the mixture to be treated with the chlorine essentially consists of the alkylaniline to be chlorinated and of sulfuric acid. In particular, the reaction mixture preferably is essentially free of organic solvents, as the presence of organic solvents may affect selectivity and/or yield of the chlorination reaction.

The process of the present invention allows a selective meta-chlorination of alkylanilines of the formula (2) in high yields and with few side products. Unreacted starting material can be recycled. The present process, thus, can be carried out in a simple manner and at low costs.

Further advantages of the present invention will be obvious from the following non-limiting examples which illustrate the present invention.

EXAMPLES

The following examples illustrate the chlorination of 2,6-dialkylanilines in the presence of sulfuric acid under various conditions in a closed (Examples 1 to 11) or an open (Examples 12 to 14) system. Gas chromatography (GC) was carried out using an Agilent 6850 apparatus and a dimethylpolysiloxane capillary as the separation column (30 m×0.32 mm×0.35 μm; 90° C., 3 K/min, 135° C., 30 K/min, 300° C.).

Example 1

13.0 g (87.1 mmol) 2,6-diethylaniline and 26.4 g (258 mmol) sulfuric acid (96% by weight) were introduced in an autoclave made of Hastelloy® HC22. The autoclave was heated to 30° C. and flushed with nitrogen to check leak-tightness. After having released the nitrogen, 6.2 g (87.4 mmol) chlorine gas were introduced into the mixture. The reaction was stirred at 30° C. for 3 h and then poured into 50 g of ice. The suspension was neutralized with 200 g of 10% aqueous sodium hydroxide. After phase separation, the aqueous layer was extracted with 75 g of ethyl acetate, and the combined organic layers were evaporated under reduced pressure to give 15.7 g of a crude product containing 94.4% of 3-chloro-2,6-diethylaniline and 4.4% of 2,6-diethylaniline as determined by gas chromatography. 3-Chloro-2,6-diethylaniline was purified by distillation.

[$C_{10}H_{14}ClN$]:
$^1$H NMR (CDCl$_3$, 500 MHz): δ 1.16 (t, J=7.5 Hz, 3H, CH$_3$), 1.23 (t, J=7.5 Hz, 3H, CH$_3$), 2.47 (q, J=7.5 Hz, 2H, CH$_2$), 2.73 (q, J=7.5 Hz, 2H, CH$_2$), 3.73 (br s, 2H, NH$_2$), 6.76 (d, J=8.3 Hz, 1H, 4-Ar—H), 6.84 (d, J=8.3 Hz, 1H, 5-Ar—H).
$^{13}$C NMR (CDCl$_3$, 500 MHz): δ 11.8, 12.6, 21.5, 23.9, 118.7, 125.0, 126.1, 126.2, 131.8, 142.8.
GC: $t_R$=15.9 min.

Example 2

Example 1 was repeated with a reaction time of 1 h. The obtained product contained (according to GC) 91.9% of 3-chloro-2,6-diethylaniline and 3.3% of starting material.

Example 3

Example 1 was repeated with a reaction time of 0.5 h. The obtained crude product contained (according to GC) 90.9% of 3-chloro-2,6-diethylaniline and 7.9% of starting material.

Example 4

Example 1 was repeated with a reaction time of 6 h and a molar ratio of Cl$_2$ to 2,6-diethylaniline of 1.05:1. The obtained crude product contained (according to GC) 94.9% of 3-chloro-2,6-diethylaniline and 1.3% of 3,5-dichloro-2,6-diethylaniline. No starting material could be detected.

Example 5

Example 1 was repeated with a molar ratio of sulfuric acid to 2,6-diethylaniline of 15:1 and a molar ratio of Cl$_2$ to 2,6-diethylaniline of 0.95:1. The reaction was carried out with stirring in the autoclave at 15° C. The obtained crude product contained (according to GC) 90.4% of 3-chloro-2,6-diethylaniline and 8.7% of starting material.

Example 6

5.0 g (33.5 mmol) of 2,6-diethylaniline and 50 g (357 mmol) of 70% sulfuric acid were introduced in an autoclave made of Hastelloy® HC22. The autoclave was heated to 30° C. and flushed with nitrogen to check leak-tightness. Having released the nitrogen, 2.3 g (32.4 mmol) of chlorine gas were introduced into the mixture. The reaction was stirred at 30° C. for 3 h and then poured into 50 g of ice. The suspension was neutralized with 90 g of 30% aqueous sodium hydroxide. Following phase separation the aqueous layer was extracted with 50 g of ethyl acetate and the combined organic layers were evaporated under reduced pressure to give 4.4 g of a crude product containing 67.9% of 3-chloro-2,6-diethylaniline and 13.6% of 2,6-diethylaniline (according to GC).

Example 7

A mixture of 5.0 g (33.5 mmol) of 2,6-diethylaniline and 6.1 g (33.2 mmol) of 3-chloro-2,6-diethylaniline in 50.8 g (497 mmol) of sulfuric acid (96% by weight) was introduced in an autoclave made of Hastelloy® HC22. The autoclave was heated to 30° C. and flushed with nitrogen to check leak-tightness. Having released the nitrogen, 2.3 g (32.4 mmol) of chlorine gas were introduced into the mixture. The reaction was stirred at 30° C. for 1 h and then poured into 50 g of ice. The suspension was neutralized with 120 g of 30% aqueous sodium hydroxide. Following phase separation the aqueous layer was extracted with 60 g of ethyl acetate and the combined organic layers were evaporated under reduced pressure to give 10.9 g of a crude product containing 92.5% of 3-chloro-2,6-diethylaniline, 3.2% of 2,6-diethylaniline, and 0.5% of 3,5-dichloro-2,3-diethylaniline (as determined by GC).

Example 8

Comparative Example 10.0 g (67.0 mmol) of 2,6-diethylaniline and 54.7 g (469 mmol) of chlorosulfonic acid were introduced in an autoclave made of Hastelloy® HC22. The autoclave was heated to 30° C. and flushed with nitrogen to check leak-tightness. Having released the nitrogen, 4.7 g (66.3 mmol) of chlorine gas were introduced to the mixture. The reaction was stirred at 30° C. for 3 h and then poured into 50 g of ice. The suspension was neutralized with 60 g of 30% aqueous sodium hydroxide. Following phase separation, the aqueous layer was extracted with 50 g of ethyl acetate, and the combined organic layers were evaporated under reduced pressure to give 12.1 g of a crude mixture containing 18.6% 3-chloro-2,6-diethylaniline and 10.5% of 3,5-dichloro-2,6-diethylaniline (according to GC).

Example 9

6.0 g (40.2 mmol) of 2,6-diethylaniline and 60.6 g (593 mmol) of sulfuric acid (96% by weight) were introduced in an autoclave made of Hastelloy® HC22. The autoclave was heated to 30° C. and flushed with nitrogen to check leak-tightness. Having released the nitrogen, 6.2 g (87.4 mmol) of chlorine gas were introduced into the mixture. The reaction was stirred at 30° C. for 3 h and then poured into 50 g of ice. The suspension was neutralized with 470 g of 10% aqueous sodium hydroxide. Following phase separation the aqueous layer was extracted with 60 g of ethyl acetate and the combined organic layers were evaporated under reduced pressure to give 7.4 g of a crude product containing 40.5% of 3-chloro-2,6-diethylaniline and 54.5% of 3,5-dichloro-2,6-diethylaniline (according to GC).

Example 10

Example 9 was repeated with a molar ratio of Cl$_2$ to 2,6-diethylaniline of 2.1:1 and a reaction temperature of 80° C. The obtained crude product contained (according to GC) 12.7% of 3-chloro-2,6-diethylaniline and 55.4% of 3,5-dichloro-2,6-diethylaniline.

Example 11

3.3 g (22.1 mmol) of 2,6-diethylaniline and 44.7 g (438 mmol) of sulfuric acid (96% by weight) were introduced in an autoclave made of Hastelloy® HC22. The autoclave was heated to 35° C. and flushed with nitrogen to check leak-tightness. Having released the nitrogen, 6.2 g (87.4 mmol) of chlorine gas were introduced into the mixture. The reaction was stirred at 35° C. for 4.5 h and then poured into 50 g of ice. The suspension was neutralized with 360 g of 10% aqueous sodium hydroxide. Following phase separation the aqueous layer was extracted with 60 g of ethyl acetate and the combined organic layers were evaporated under reduced pressure to give 4.7 g of a crude product containing 8.3% of 3-chloro-2,6-diethylaniline and 71.2% of 3,5-dichloro-2,6-diethylaniline (according to GC).

[$C_{10}H_{13}Cl_2N$]:
$^1$H NMR (($CD_3$)$_2$SO, 400 MHz): δ 1.02 (t, J=7.5 Hz, 6H, $CH_3$), 2.66 (q, J=7.5 Hz, 4H, $CH_2$), 5.19 (br s, 2H, $NH_2$), 6.66 (s, 1H, 4-Ar—H).
GC: $t_R$=17.6 min.

Example 12

A round bottom flask equipped with a reflux condenser and a stirring bar was charged with 5.0 g (33.5 mmol) of 2,6-diethylaniline and 50.8 g (497 mmol) of sulfuric acid (96% by weight) and heated to 80° C. Within 2 h 23.5 g (331 mmol) of chlorine gas were passed through the reaction solution using a dip pipe. The resulting mixture was stirred for another 3 h at 80° C. and then poured into 50 g of ice. The suspension was neutralized with 130 g of 30% aqueous sodium hydroxide and 90 g of ethyl acetate were added. Following phase separation, the organic layer was evaporated under reduced pressure to give 5.6 g of a crude product, containing of 94.8% of 3-chloro-2,6-diethylaniline and 2.4% of 2,6-diethylaniline (according to GC). The crude product could be purified by distillation.

Example 13

Example 12 was repeated with a molar ratio of $Cl_2$ to 2,6-diethylaniline of 5:1. The obtained crude product contained (according to GC) 60.4% of 3-chloro-2,6-diethylaniline and 37.8% of starting material.

Example 14

Example 12 was repeated with a molar ratio of sulfuric acid to 2,6-diethylaniline of 2:1 and a molar ratio of $Cl_2$ to 2,6-diethylaniline of 5:1. The obtained crude product contained (according to GC) 16.3% of 3-chloro-2,6-diethylaniline and 71.3% of starting material.

Details and results of Examples 1 to 14 are summarized in Table 1 below. The abbreviation RRT means relative retention time.

Examples 1 to 7 show that monochlorination in meta-position of 2,6-dialkylanilines in a closed system can be effected in good yields with a selectivity of more than 90%. The yield may be improved with higher concentrated sulfuric acid and/or with an increased molar ratio of sulfuric acid to dialkylaniline. The reaction can efficiently be carried out at low temperatures. Monochlorination is obtained by adjusting the molar ratio of $Cl_2$ to dialkylaniline to about stoichiometric amounts. From Example 7 it will be seen that selective monochlorination rather than dichlorination takes place even if a mixture of dialkylaniline and 3-chloro-2,6-dialkylaniline is used as the starting material.

Comparative Example 8 demonstrates that the use of a sulfuric acid derivative such as chlorosulfonic acid instead of sulfuric acid results in a mixture of mono- and di-chlorinated products in low yields.

Examples 9 to 11 show that the di-meta-chlorinated product becomes the main product if chlorination is carried out with chlorine in excess or at higher temperatures. No para-chlorinated product could be detected demonstrating the high selectivity of the present process.

A selectivity of more than 90% for chlorination in meta-position could also be achieved when an open reaction system was used (Examples 12 to 14). Conversion of the starting material increases with increasing amounts of chlorine gas passed through the starting mixture.

Example 15

Example 1 was repeated using 10.0 g (67.0 mmol) of 2-isopropyl-6-methylaniline instead of 2,6-diethylaniline as the substrate to evaluate the selectivity of the chlorination process with an asymmetrically substituted 2,6-dialkylaniline. The crude product obtained contained 3-chloro-6-isopropyl-2-methylaniline and 3-chloro-2-isopropyl-6-methylaniline as a 4:1 mixture (according to GC), thus demonstrating that also in case of asymmetrically substituted dialkylanilines only the meta-positions of the aromatic amine

TABLE 1

| | | Reaction | | | | Proportion (%) in Product Mixture[1] | | | |
|---|---|---|---|---|---|---|---|---|---|
| Ex. | Acid | Molar ratio acid:aniline | Molar ratio $Cl_2$:aniline | temperature (° C.) | Time (h) | 2,6-DEA | 3-Cl-2,6-DEA | 4-Cl-2,6-DEA | 3,5-diCl-2,6-DEA |
| Closed system (autoclave) | | | | | | | | | |
| 1 | 96% $H_2SO_4$ | 3:1 | 1:1 | 30 | 3 | 4.4 | 94.4 | 0.0 | 0.3 |
| 2 | 96% $H_2SO_4$ | 3:1 | 1:1 | 30 | 1 | 3.3 | 91.9 | 0.0 | 0.3 |
| 3 | 96% $H_2SO_4$ | 3:1 | 1:1 | 30 | 0.5 | 7.9 | 90.9 | 0.0 | 0.3 |
| 4 | 96% $H_2SO_4$ | 3:1 | 1.05:1 | 30 | 6 | 0.0 | 94.9 | 0.0 | 1.3 |
| 5 | 96% $H_2SO_4$ | 15:1 | 0.95:1 | 15 | 3 | 8.7 | 90.4 | 0.0 | 0.1 |
| 6 | 70% $H_2SO_4$ | 10.7:1 | 0.97:1 | 30 | 3 | 67.9 | 13.6 | 1.5 | 0.1 |
| 7[2] | 96% $H_2SO_4$ | 15:1 | 0.97:1 | 30 | 1 | 3.2 | 92.5 | 0.0 | 0.5 |
| 8 | $ClSO_3H$ | 7:1 | 1:1 | 30 | 3 | 0.0 | 18.6 | 0.0 | 10.5 |
| 9 | 96% $H_2SO_4$ | 15:1 | 2.2:1 | 30 | 3 | 0.0 | 40.5 | 0.0 | 54.5 |
| 10 | 96% $H_2SO_4$ | 15:1 | 2.1:1 | 80 | 3 | 0.0 | 12.7 | 0.0 | 55.4 |
| 11 | 96% $H_2SO_4$ | 20:1 | 4.0:1 | 35 | 4.5 | 0.0 | 8.3 | 0.0 | 71.2 |
| Open system | | | | | | | | | |
| 12 | 96% $H_2SO_4$ | 15:1 | 10:1 | 80 | 3 | 2.4 | 94.8 | 0.8 | 0.0 |
| 13 | 96% $H_2SO_4$ | 15:1 | 5:1 | 80 | 3 | 37.8 | 60.4 | 0.0 | 0.2 |
| 14 | 96% $H_2SO_4$ | 2:1 | 5:1 | 80 | 3 | 71.3 | 16.3 | 0.0 | 0.0 |

[1]The proportions of the compounds in the product mixture are calculated on basis of the areas of the respective peaks in a gas chromatogram (2,6-DEA = 2,6-diethylaniline, $t_R$ = 10.1 min, RRT = 0.62; 3-Cl-2,6-DEA = 3-chloro-2,6-diethylaniline, $t_R$ = 15.9 min, RRT = 1.00; 3,5-diCl-2,6-DEA = 3,5-dichloro-2,6-diethylaniline, $t_R$ = 17.6 min, RRT = 1.11; 4-Cl-2,6-DEA = 4-chloro-2,6-diethylaniline, $t_R$ = 16.4 min, RRT = 1.03)
[2]Mixed starting material: 2,6-dialkylaniline and 3-chloro-2,6-dialkylaniline.

are chlorinated, with chlorination apparently being predominant at the position sterically less hindered by the adjacent alkyl substituent.

Example 16

Comparative Example

According to U.S. Pat. No. 4,401,833 the following comparative example to provide 4-chloro-2,6-diethylaniline was performed:

In a glass reactor, 2,6-diethylaniline (50 g, 332 mmol) was dissolved in a mixture of toluene (122 g, 1.33 mol) and ethanol (15 g, 332 mmol). HCl gas (15 g, 332 mmol) was introduced at room temperature. After saturation was reached, chlorine gas (47 g, 663 mmol) was passed through the resulting suspension within 4 h.

After termination of the chlorination process the suspension was neutralized with 40% aqueous sodium hydroxide (107 g solution, 1.06 mol). After phase separation the aqueous phase was extracted with toluene, and the combined organic layers were evaporated to give the crude product as a mixture of 22% 2,6-diethylaniline and 53% 4-chloro-2,6-diethylaniline (according to GC).

Thus, the yield, relative to the amount of 2,6-diethylaniline reacted, was 68%.

The above examples demonstrate that the chlorination process of the present invention is a highly effective method for selectively chlorinating anilines in meta position relative to the aromatic amino group.

The invention claimed is:

1. A process for the preparation of chlorinated alkylanilines of the formula (1)

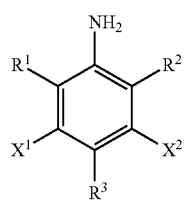

(1)

wherein $R^1$ and $R^2$ independently are an alkyl group, and $R^3$ is H or an alkyl group, and $X^1$ and $X^2$ independently are H or Cl, with the proviso that at least one of $X^1$ and $X^2$ is Cl, or a sulfuric acid salt thereof, said process comprising the steps of:

(a) providing an alkylaniline of the formula (2)

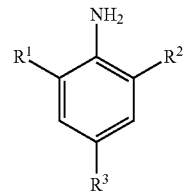

(2)

wherein $R^1$, $R^2$ and $R^3$ are as defined above, in the anilinium form in a mixture with sulfuric acid as solvent; and (b) treating the mixture of step (a) with chlorine ($Cl_2$) to obtain the alkylaniline of the formula (1) in the form of a sulfuric acid salt, optionally followed by treatment with a base to obtain the free alkylaniline.

2. The process of claim 1, wherein $R^3$ is H.

3. The process of claim 1, wherein $R^1$ and $R^2$ are the same.

4. The process of claim 1, wherein the reaction is carried out in a closed system.

5. The process of claim 1, wherein the reaction is carried out in an open system.

6. The process of claim 1, wherein the reaction is carried out at a temperature of from 5° C. to 120° C.

7. The process of claim 6, wherein the reaction is carried out at a temperature of from 10° C. to 100° C.

8. The process of claim 1, wherein the sulfuric acid has an $H_2SO_4$ concentration of at least 70% by weight.

9. The process of claim 1, wherein the sulfuric acid has an $H_2SO_4$ concentration of at least 85% by weight.

10. The process of claim 1, wherein the sulfuric acid has an $H_2SO_4$ concentration of at least 95% by weight.

* * * * *